United States Patent [19]

Elthes et al.

[11] Patent Number: 4,704,281

[45] Date of Patent: Nov. 3, 1987

[54] MEDICINAL VEGETABLE COMPOSITION FOR TREATING SOME HEPATIC AND BILIARY DISEASES

[75] Inventors: Ludovic L. Elthes; Aristina Elthes, both of Oradea, Romania

[73] Assignee: Directia Sanitara a Judetului Neamt Laboratoarele Plantavorel, Piatra Meant, Romania

[21] Appl. No.: 773,004

[22] PCT Filed: Jan. 27, 1985

[86] PCT No.: PCT/RO85/00001

§ 371 Date: Nov. 18, 1985

§ 102(e) Date: Nov. 18, 1985

[87] PCT Pub. No.: WO85/03229

PCT Pub. Date: Aug. 1, 1985

[30] Foreign Application Priority Data

Jan. 27, 1984 [RO] Romania ................................ 113423

[51] Int. Cl.$^4$ ............................................. A61K 35/78
[52] U.S. Cl. .................................. 424/195.1; 514/877; 514/894
[58] Field of Search .................... 424/195.1; 514/877, 514/894

[56] References Cited

PUBLICATIONS

Steinmetz, Cotex Vegetabilis, 425 & 426, 1957.
Green, Universal Herbal or Bot., Med and Agri. Dictionary, pp. 502–503, 1824.
Flora: Republicii Populare Romine, Savulescu, vol. V, (1957).

*Primary Examiner*—J. R. Brown
*Assistant Examiner*—John W. Rollins, Jr.
*Attorney, Agent, or Firm*—Karl F. Ross; Herbert Dubno

[57] ABSTRACT

The medicinal vegetable composition for treating some hepatobiliary diseases, according to the invention, contains an association of the plants *Epilobium hirsutum* L., *Chamaenerion palustre* Schreb. and *Chamaenerion angustifolium* (L.)Scop., their ratio being 15 to 40: 20 to 50: 35 to 80, respectively, the ratio being calculated based on 100 g of vegetable material.

2 Claims, No Drawings

MEDICINAL VEGETABLE COMPOSITION FOR TREATING SOME HEPATIC AND BILIARY DISEASES

The present invention refers to a medicinal vegetable composition for treating functional or organic hepatic and biliary diseases, in order to restore the basic hepatic function.

Some drugs as "Essentiale","Purinor"—"Produse farmaceutice folosite în practica medicinală" 1981 p. 391—"Agenda medicală" 1981, p. 666 are known as useful drugs to restore the liver metabolism.

Compositions are also known that are used in hepatic and biliary diseases which contain active principles from *Berberis vulgaris* L. alone or associated—RSR 66691 and, 63127 patents, or vegetable extracts from the plants *Chelidonium majus* L. and *Hypericum perforatum* L. associated with products as virgin wax, honey larva triturate and propolis powder—RSR 80826 patent.

The present invention relates to a new composition to treat hepatic and biliary diseases and which contains an association of the plants *Epilobium hirsutum* L., *Chamaenerion palustre* Schreb. and *Chamaenerion angustifolium* (L) Scop. their rates being of 15 to 40:20 to 50:35 to 80, the rates being calculated based upon 100 g of vegetable material.

Below are given two examples of obtaining the vegetable medicinal composition according to the invention.

EXAMPLE 1

The composition contains the aerial, underground and subaquatic parts of the plants: 20 g of *Epilobium hirsutum* L., 40 g of *Chamaenerion palustre* Schreb., 40 of *Chamaenerion angustifolium* (L) Scop.

The vegetable composition is obtained by mixing the aqueous decoction of the hard parts and roots with the aqueous infusion, of their aerial parts. The aqueous decoction is obtained by boiling the hard parts of the plants in the rates stated for 7–14 min. The mixture consists of putting ⅔ hard parts and roots with ⅓ leaves, flowers and seeds.

The solution thus obtained is administrated 2–3 times/day each of 100–250 g per os/day, 30–45 min. before meals in biliary dyskinesia, chronic hepatic diseases and calculus diseases.

EXAMPLE 2

The composition consists of the aerial, underground and subaquatic parts of the plants: 10 g of *Epilobium hirsutum* L., 30 g of *Chamaenerion palustre* Schreb., 60 g of *Chamaenerion angustifolium* (L) Scop.

The decoction from the hard and ligneous parts of the plants is made under the same condition as in example 1, and the other parts of the plants are directly infused in the decoction. The rates of the hard parts and roots of the plants, in relation to the other parts, are the same as in example 1. The administration is also the same.

The above composition is intended to treat functional or organic acute and chronic hepatic and biliary diseases, namely biliary dyskinesia, calculus biliary diseases, chronic hepatopathies: persistent chronic hepatitis, aggresive chronic hepatitis, compensated biliary cirrhosis, chronic pancreatitis, biliary calculus.

The vegetable composition according to the invention has the following advantages:

- it has a very good digestive tolerance.
- it definitely improves bile secretion, the dynamics of bile elimination into the duodenum, realizing an optimum drainage required by digestion.
- it helps significantly to regenerate the liver cells, and increases the detoxifying capacity of liver.
- it improves obviously the immunopathologic processes in chronic hepatic diseases.
- it has strong roborant effects upon the body.

We claim:

1. A pharmaceutical composition for the treatment of biliary dyskinesia, biliary calculus, chronic hepatopathies, chronic hepatitis, aggressive chronic hepatitis, compensated biliary cirrhosis, or pancreatitis, which comprises as active ingredients:
   (a) 15 to 30 parts by weight of roots, stems, leaves, flowers, and seeds of the plant *Epilobium hirsutum* L.;
   (b) 20 to 50 parts by weight of roots, stems, leaves, flowers, and seeds of the plant *Chamaenerion palustre* Schreb.; and
   (c) 35 to 80 parts by weights of roots, stems, leaves, flowers, and seeds of the plant *Chamaenerion angustifolium* L Scop; the quantities based on 100 grams of vegetable composition, and the ratio of the root and stem, in each, to the leaves, flowers, and seeds is 2:1; in solution in a pharmaceutically acceptable carrier in the form of water.

2. A method of treating a patient for biliary dyskinesia, biliary calculus, chronic hepatopathies, chronic hepatitis, aggressive chronic hepatitis, compensated biliary cirrhosis, or pancreatitis, which comprises the step of orally administering to said patient in need of said treatment a therapeutically effective amount of the pharmaceutical composition defined in claim 1.

* * * * *